United States Patent [19]

Fäh et al.

[11] 4,287,347
[45] Sep. 1, 1981

[54] PROCESS FOR PRODUCING 2,3,5-TRICHLOROPYRIDINE

[75] Inventors: Hansjakob Fäh, Ettingen; Alfred Grieder, Böckten, both of Switzerland

[73] Assignee: Ciba-Geigy Corporation, Ardsley, N.Y.

[21] Appl. No.: 148,849

[22] Filed: May 12, 1980

[51] Int. Cl.$^3$ .................................... C07D 213/02
[52] U.S. Cl. ............................................ 546/345
[58] Field of Search ............................... 546/345

[56] References Cited

PUBLICATIONS

Rath, Justus Liebigs Ann. der Chemie, Band 486, pp. 74–79, Verlag Pub., Berlin, (1931).
Cava et al., Journal of Organic Chemistry, vol. 23, pp. 1614–1616, (1958).
Camps et al., Archiv der Pharmazie, Band 240, pp. 350–351, (1902).

Primary Examiner—Alan L. Rotman

Attorney, Agent, or Firm—Karl F. Jorda

[57] ABSTRACT

Production of 2,3,5-trichloropyridine by reacting 3,5-dichloro-2-pyridone at 30° to 150° with phosgene in the presence of an N,N-disubstituted formamide of the formula

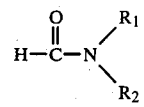

in which $R_1$ and $R_2$ can be identical or different and are each an alkyl group having 1 to 4 carbon atoms, or $R_1$ and $R_2$ together with the nitrogen atom form the pyrrolidino, piperidino or morpholino, and in the presence of an inert solvent.

2,3,5-trichloropyridine is a valuable intermediate for producing herbicidally active α-[4-(3′,5′-dichloropyrid-2-yloxy)-phenoxy]-alkanecarboxylic acids and derivatives thereof.

1 Claim, No Drawings

PROCESS FOR PRODUCING 2,3,5-TRICHLOROPYRIDINE

The present invention relates to a process for producing 2,3,5-trichloropyridine.

2,3,5-Trichloropyridine is a valuable intermediate for producing herbicidally active α-[4-(3',5'-dichloropyrid-2-yloxy)-phenoxy]-alkanecarboxylic acids and derivatives thereof. The production and use of such α-[4-(3',5'-dichloropyrid-2-yloxy)-phenoxy]-alkanecarboxylic acids and derivatives thereof are described for example in the U.S. Pat. No. 4,092,151.

The production of 2,3,5-trichloropyridine by reaction of N-methyl-3,5-dichloro-2-pyridone with phosgene as solvent is known. The process comprises introducing N-methyl-3,5-dichloro-2-pyridone into a toluene solution of phosgene, and heating the mixture in a closed system for 3 hours at 150° C. 2,3,5-Trichloropyridine is obtained in this manner in a yield of about 90% of theory (Ann. Chem. 486, 78–79 (1931)). The N-methyl-3,5-dichloro-2-pyridone required as starting material for carrying out this process is obtainable by reaction of 2-aminopyridine with potassium nitrite in a sulfuric acid solution to 2-pyridone (Arch. Pharm. 240, 250 (1903)), chlorination of this to give 3,5-dichloro-2-pyridine (J. Org. Chem. 23, 1614 (1958)), and subsequent methylation thereof (Ann. Chem. 486, 74 (1931).

The known process is disadvantageous in so far as the 3,5-dichloro-2-pyridone obtained by chlorination of 2-pyridone has firstly to be converted into N-methyl-3,5-dichloro-2-pyridone, and the N-methyl group of this is removed again in the subsequent reaction with phosgene to give 2,3,5-trichloropyridine. In this process, there is thus intermediately introduced a group which is not present at all in the final product. This is uneconomical with respect to the necessity of having to carry out an additional process step, with respect to the costs associated with that, with respect to the losses in yield resulting from this additional step, and finally with respect to the consumption of chemicals which do not contribute towards the structural synthesis of the end product. Furthermore, the high reaction temperature at which the process is performed necessitates carrying out the reaction in a closed system under pressure, and as a result of this there is a considerable increase in the expenditure on equipment required to carry out the process on a large commercial scale.

The aim of the present invention therefore is to avoid the disadvantages of the known procedure, and to provide a process by which 2,3,5-trichloropyridine can be produced on a commercial scale in a simple and economic manner.

The proposal according to the present invention is to produce 2,3,5-trichloropyridine by reacting 3,5-dichloro-2-pyridone at 30°–150° C. with phosgene in the presence of an N,N-disubstituted formamide of the formula

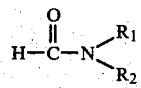  (I)

in which $R_1$ and $R_2$ can be identical or different and are each an alkyl group having 1–4 carbon atoms, or $R_1$ and $R_2$ together with the nitrogen atom form the pyrrolidino, piperidino or morpholino group, and in the presence of an inert solvent.

The reaction of 3,5-dichloro-2-pyridone is performed within the above-given temperature range of 30°–150° C., preferably at 50°–90° C. The reaction is performed as a rule under normal pressure. It may be necessary to carry out the reaction in a closed system under pressure only when a relatively low-boiling solvent is used and a high reaction temperature applied, for example a temperature in the range of 100°–150° C.

Suitable solvents in which the process according to the invention can be performed are in general those solvents which under the reaction conditions are inert to the reactants. Suitable solvents are in particular: aromatic hydrocarbons, such as benzene, toluene or xylene; aliphatic hydrocarbons, such as hexane, heptane or petroleum ether; cycloaliphatic hydrocarbons, such as cyclopentane and cyclohexane; halogenated aromatic hydrocarbons, such as chlorobenzene or o-dichlorobenzene; halogenated aliphatic hydrocarbons, such as methylene chloride, chloroform, carbon tetrachloride, 1,2-dichloroethane and trichloroethylene, as well as aliphatic carboxylic acid esters, such as ethyl acetate and isopropyl acetate. A preferred solvent is toluene.

Suitable N,N-disubstituted formamides are N,N-dimethylformamide, N,N-diethylformamide, N,N-dipropylformamide, N,N-dibutylformamide, N-methyl-N-butylformamide, as well as N-formylpyrrolidine, N-formylpiperidine and N-formylmorpholine. A preferred N,N-disubstituted formamide is N,N-dimethylformamide. The N,N-disubstituted formamides are used in amounts of 0.01–1.0 mol per mol of 3,5-dichloro-2-pyridone, preferably 0.05 to 0.15 mol per mol of 3,5-dichloro-2-pyridone.

Phosgene is used according to the invention generally in at least an equimolar amount or in excess. The amount advantageously used is 1.0 to 1.5 mols of phosgene per mol of 3,5-dichloro-2-pyridone. The amount preferably used is 1.0 to 1.3 mols of phosgene per mol of 3,5-dichloro-2-pyridone. After completion of the reaction, the unreacted phosgene is reacted with an aqueous caustic solution, such as with an aqueous sodium hydroxide solution or with aqueous ammonia.

The reaction of 3,5-dichloro-2-pyridone with phosgene takes as a rule 1–5 hours, and in most cases it is completed in 2–4 hours.

According to a preferred embodiment of the process of the invention, 3,5-dichloro-2-pyridone is suspended in toluene, the water present is separated by azeotropic distillation, 0.05–0.15 mol of N,N-dimethylformamide per mol of 3,5-dichloro-2-pyridone is added, and 1.0–1.3 mols of phosgene per mol of 3,5-dichloro-2-pyridone are introduced at 75°–80° C. After the addition of phosgene has been completed, the reaction mixture is allowed to react for a further one hour at 75°–80° C., and the excess phosgene is subsequently reacted with aqueous ammonia. The phases are afterwards separated, the solvent is distilled off from the organic phase, and 2,3,5-trichloropyridine is obtained as a melt.

It becomes possible by the process according to the invention to produce 2,3,5-trichloropyridine on a commercial scale in a simple and economic manner. The process avoids the N-methylation of 3,5-dichloro-2-pyridone which the known process necessitates, and can be performed under considerably milder conditions. The total yield is increased, and the necessary expenditure on equipment to carry out the process is reduced.

The process according to the invention is further illustrated by the following Example.

EXAMPLE 82.0 kg of 3,5-dichloro-2-pyridone, 330 kg of toluene and 3.8 kg of N,N-dimethylformamide are placed into a 500 liter enamelled vessel. The mixture is then heated with stirring to 75°–80° C., and at this temperature 60.0 kg of phosgene are introduced in the course of 2–3 hours. After completion of the addition of phosgene, stirring is continued at 75°–80° C. for 1 hour. The reaction mixture is afterwards cooled to 20°–25° C., and is subsequently stirred up with 12.0 kg of 25% aqueous ammonia. After separation of the aqueous phase, the toluene is distilled off at normal pressure. The yield as residue is 92.0 kg of 2,3,5-trichloropyridine (95%) [96% of theory] in the form of a melt, which solidifies on cooling. The product melts at 47°–48° C.

What is claimed is:

1. A process for producing 2,3,5-trichloro-pyridine which comprises suspending in a mixture of toluene and water, 3,5-dichloro-pyridone, the water present is separated by azeotropic distillation, adding 0.05–0.15 mol of N,N-dimethylformamide per mol of 3,5-dichloro-2-pyridone introducing, 1.0–1.3 mols of phosgene per mol of 3,5-dichloro-2-pyridone at 75°–80° C., stirring the reaction mixture further for 1 hour, reacting the excess phosgene with aqueous ammonia, separating the phases, and obtaining from the organic phase, after removal of the solvent by distillation, the formed 2,3,5-trichloro-pyridine in the form of a melt.

* * * * *